(12) United States Patent
König

(10) Patent No.: US 11,740,175 B2
(45) Date of Patent: Aug. 29, 2023

(54) METHOD AND DEVICE FOR COMPENSATING TEMPERATURE GRADIENT EFFECTS

(71) Applicant: TDK Corporation, Tokyo (JP)

(72) Inventor: Matthias König, Munich (DE)

(73) Assignee: TDK Corporation, Tokyo (JP)

( * ) Notice: Subject to any disclaimer, the term of this patent is extended or adjusted under 35 U.S.C. 154(b) by 115 days.

(21) Appl. No.: 17/504,267

(22) Filed: Oct. 18, 2021

(65) Prior Publication Data

US 2022/0120666 A1   Apr. 21, 2022

(30) Foreign Application Priority Data

Oct. 19, 2020   (DE) .......................... 102020127455.6

(51) Int. Cl.
  *G01N 21/03*   (2006.01)
  *G01N 21/74*   (2006.01)
  *G01N 21/61*   (2006.01)

(52) U.S. Cl.
  CPC ......... *G01N 21/0332* (2013.01); *G01N 21/61* (2013.01); *G01N 21/74* (2013.01); *G01N 2021/745* (2013.01)

(58) Field of Classification Search
  CPC .... G01N 21/0332; G01N 21/74; G01N 21/61; G01N 21/27; G01N 21/783; G01N 21/3504; G01N 21/274; G01N 2021/745; G01N 2201/1211; G01N 2201/12792; G01N 33/0006
  USPC .................. 356/432–440; 250/343–345, 349
  See application file for complete search history.

(56) References Cited

U.S. PATENT DOCUMENTS

| 7,244,939 B2* | 7/2007 | Stuttard ............. G01N 21/3504 |
| | | 250/343 |
| 2013/0301052 A1* | 11/2013 | MacGregor ........ G01N 33/0006 |
| | | 356/437 |
| 2018/0348311 A1* | 12/2018 | Voss ........................ G01F 23/74 |
| 2020/0348134 A1* | 11/2020 | Katingari .............. G01P 15/125 |

* cited by examiner

Primary Examiner — Hoa Q Pham
(74) Attorney, Agent, or Firm — Slater Matsil, LLP

(57) ABSTRACT

In an embodiment a method for compensating a temperature gradient effect for gas concentration sensors includes variating a temperature gradient, measuring a variation of gas concentration depending on the variation of the temperature gradient, analysing a dependence of the gas concentration and the temperature gradient for setting up an error correction function and applying the error correction function to correct measured values of the gas concentration.

5 Claims, 4 Drawing Sheets

- CO2 cal [ppm] - Plot 0
- CO2 gradient eliminated [ppm] - Plot 0
- T [°C]- Plot 0

METHOD AND DEVICE FOR COMPENSATING TEMPERATURE GRADIENT EFFECTS

CROSS-REFERENCE TO RELATED APPLICATIONS

This application claims priority to German Patent Application No. 102020127455.6, filed on Oct. 19, 2020, which application is hereby incorporated herein by reference.

TECHNICAL FIELD

Special types of gas sensors, e.g., thermal conductivity type sensors can show a temperature gradient dependence. That means that the output signal of the gas sensor not only depends on the gas concentration, e.g., $CO_2$ but also depends on the change rate (gradient) of the temperature.

BACKGROUND

In the state of the art such a behavior is not compensated. Or alternatively, a measurement unit is heated to a constant temperature so that no gradient will occur.

SUMMARY

Embodiments provide a method for compensating temperature gradient effects for gas concentration sensors comprising the following steps:
- variating a temperature gradient,
- measuring the variation of gas concentration depending on the variation of the temperature gradient,
- analysing the dependence of gas concentration and temperature gradient for setting up an error correction function,
- applying the error correction function to correct measured values of gas concentration.

In one embodiment the error correction function is a linear function.

In one embodiment the dependence of gas concentration and temperature gradient is analysed by a neuronal network.

Further embodiments provide a device for measuring gas concentrations independent of a temperature gradient comprising:
- a sensor unit measuring gas concentrations,
- an analysing unit arranged to analyse the dependence of gas concentration on the temperature gradient during calibration of the sensor unit in order to set up an error correction function and to apply the error correction function to measured values of gas concentration after calibration is completed.

In one embodiment the analysing unit comprises a neuronal network analysing the dependence of gas concentration on the temperature gradient.

BRIEF DESCRIPTION OF THE DRAWINGS

In the following the invention is exemplarily described by using figures. The invention is not limited to the described examples. The figures show.

DETAILED DESCRIPTION OF ILLUSTRATIVE EMBODIMENTS

As mentioned in the introduction special types of gas sensors, e.g., thermal conductivity type sensors can show a temperature gradient dependence.

Figure 1:
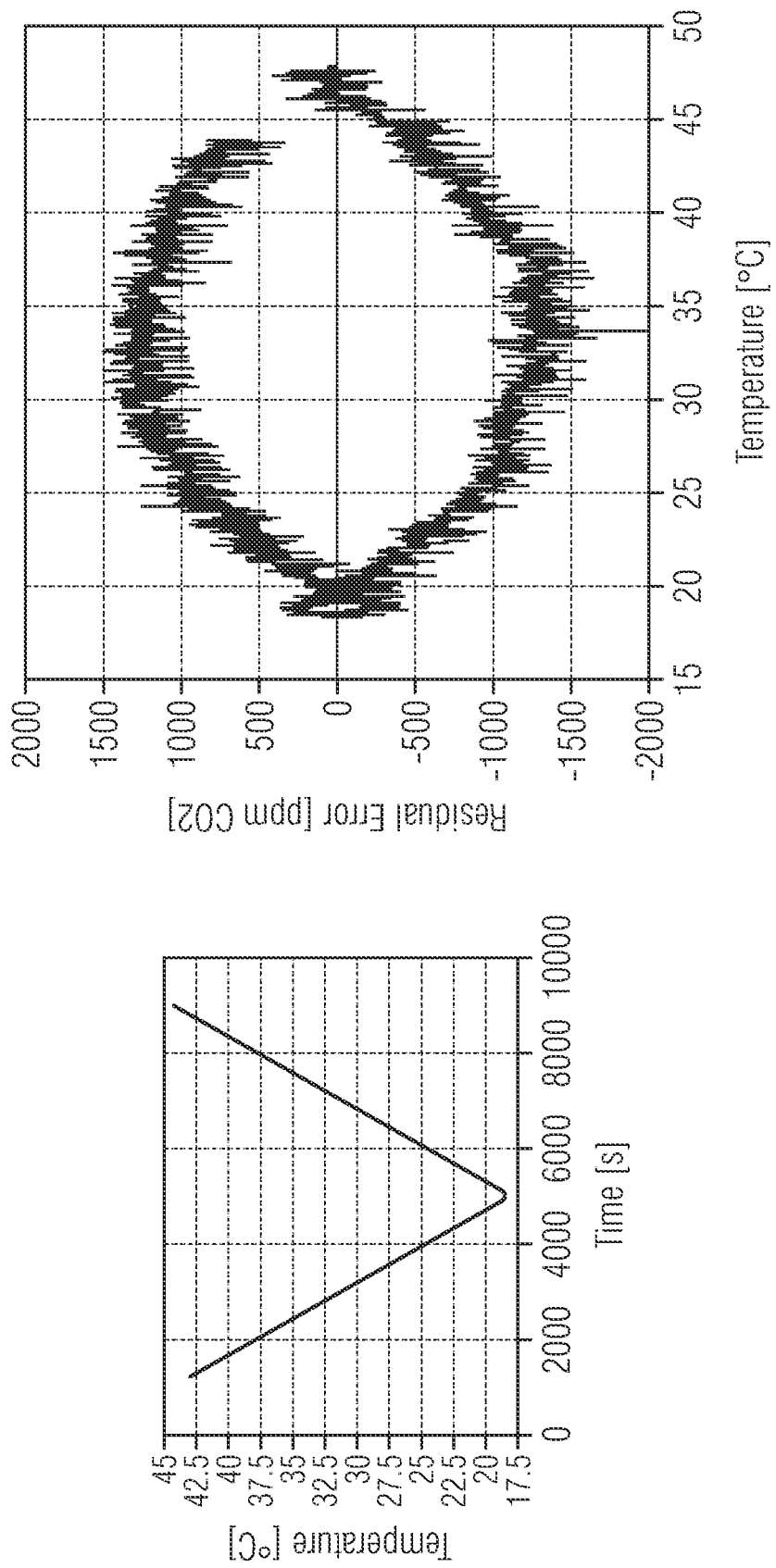
FIG. 1 shows a temperature vs time curve and a residual error vs temperature curve of a measurement by a $CO_2$ thermal conductivity gas sensor.

FIG. 1 shows such a dependence, for example. The left diagram shows the temperature sweep that is applied to an exemplary sensor. On the right diagram the influence of the temperature to a $CO_2$ concentration output signal (or any another gas concentration output signal) is shown. It is clear that the output signal does not depend on the temperature. Instead it seems to depend on the gradient of the temperature. In embodiments a method is discussed how to compensate for this behavior.

The first step to cancel such a temperature gradient dependence is to estimate the gradient error/drift (error of the gas concentration value in dependence on the temperature gradient) and subtract it from the output signal (value of gas concentration).

Figure 2:
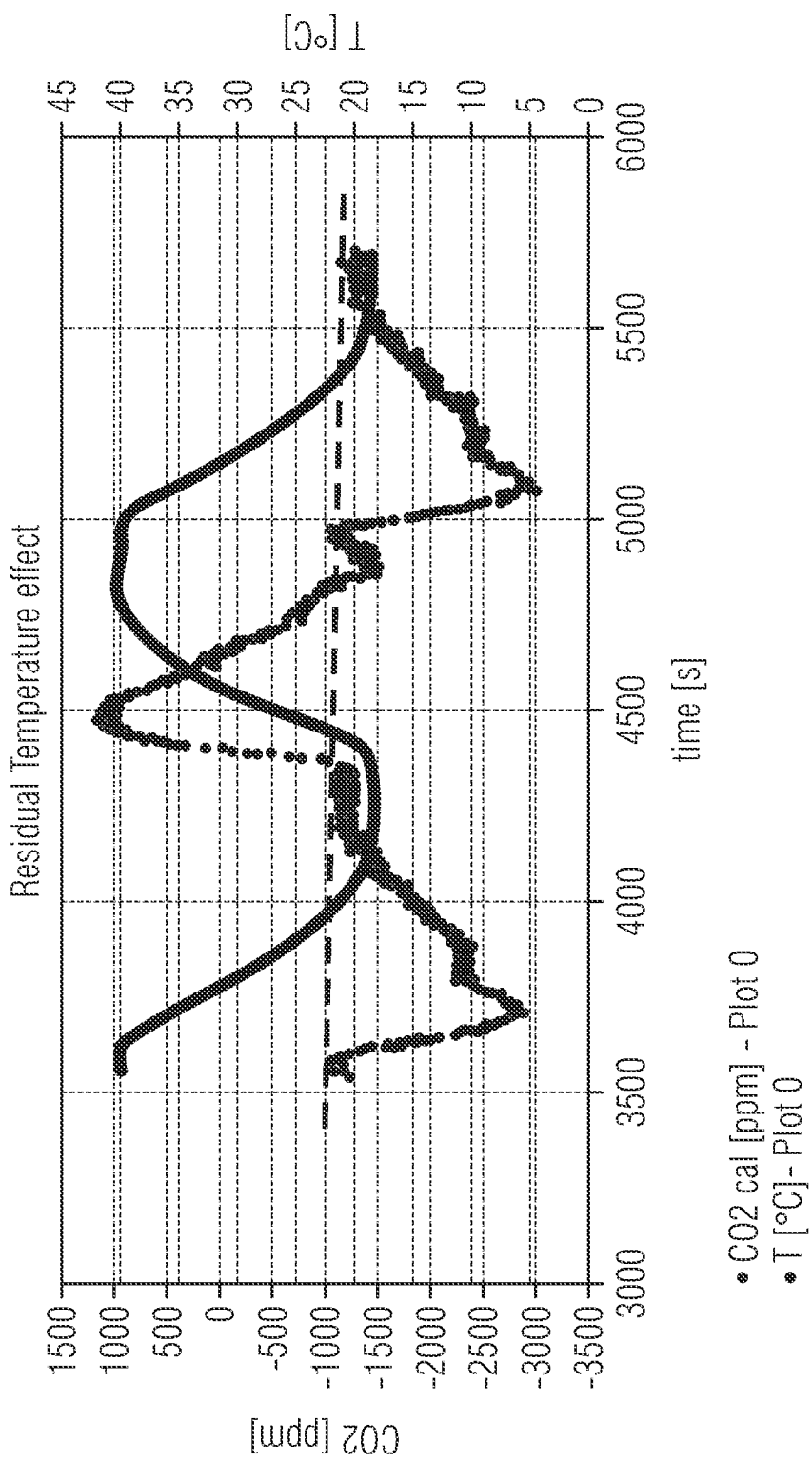
FIG. 2 shows the $CO_2$ concentration output signal during a temperature sweep.

FIG. 2 shows the $CO_2$ concentration output signal during a temperature sweep. The gradient error behavior becomes clear. The blue curve shows the temperature that is changed during the experiment. The orange curve shows the gas sensor output signal (gas concentration). If the blue curve is flat the output signal is stable at −1000 ppm (green curve: There is a little temporal drift as well). Note how the sign of the gradient influences the output signal: In case of a negative gradient a negative gradient error occurs; In case of a positive gradient a positive gradient error occurs.

The same data ($CO_2$ output signal) can be plotted vs the temperature gradient. This was done for a different sample in FIG. 3.

Figure 3:
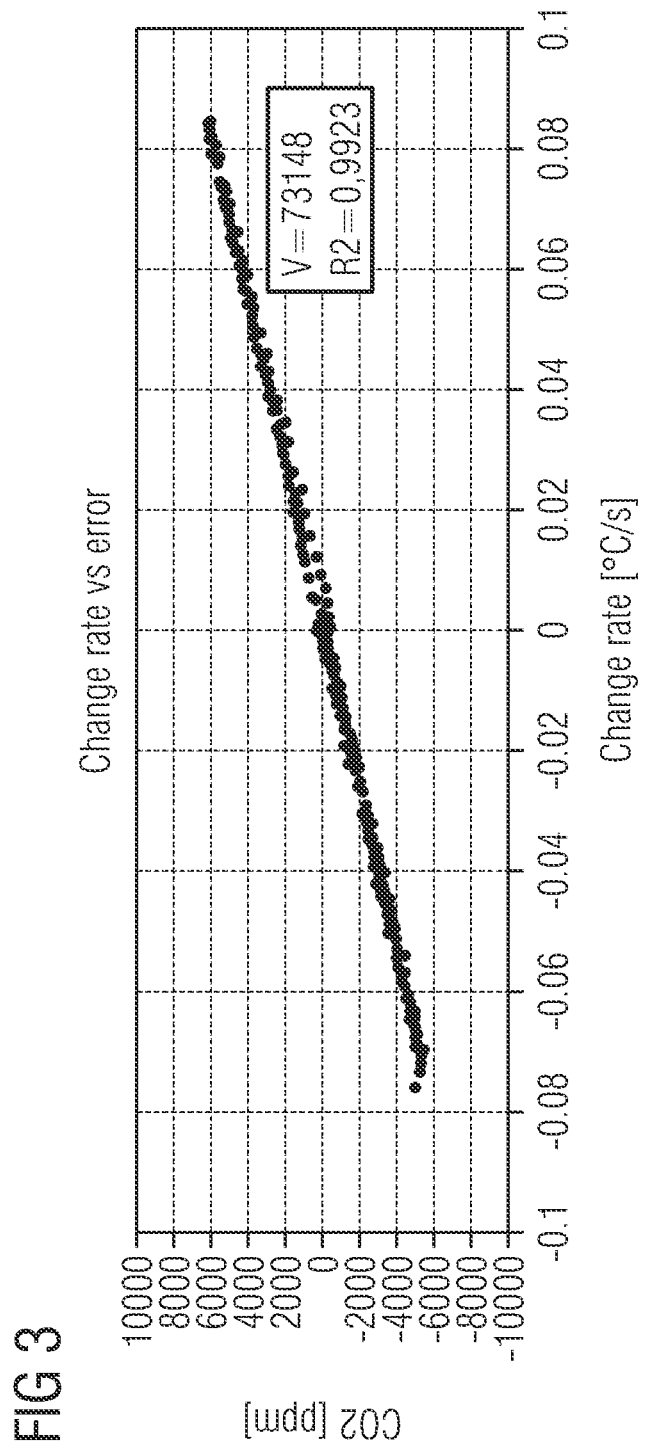
FIG. 3 shows similar data like shown in FIG. 2 but measured by a different sensor. The error of the output signal vs the temperature change rate is shown.

The data shown in FIG. 3 are similar to the data in FIG. 2 but measured by a different sensor. The error of the output signal vs the temperature change rate (temperature gradient) is shown.

In FIG. 3 the linear dependence of the gradient error becomes visible. During a calibration procedure the slope "A" of the gradient error is measured. The gas concentration output signal can then be correct by using the following error correction function:

$$c(CO_2 \text{ corrected}) = c(CO_2 \text{ measured}) - f.$$

Herein, "c" is the concentration of $CO_2$ and "f" is the gradient error. The gradient error can be calculated by $$f = \text{gradient}(T) \times A.$$

Herein, "gradient(T)" is the temperature gradient.

By applying the error correction function to the measured concentration values a much more stable signal is received. The result can be seen in FIG. 4.

Figure 4:
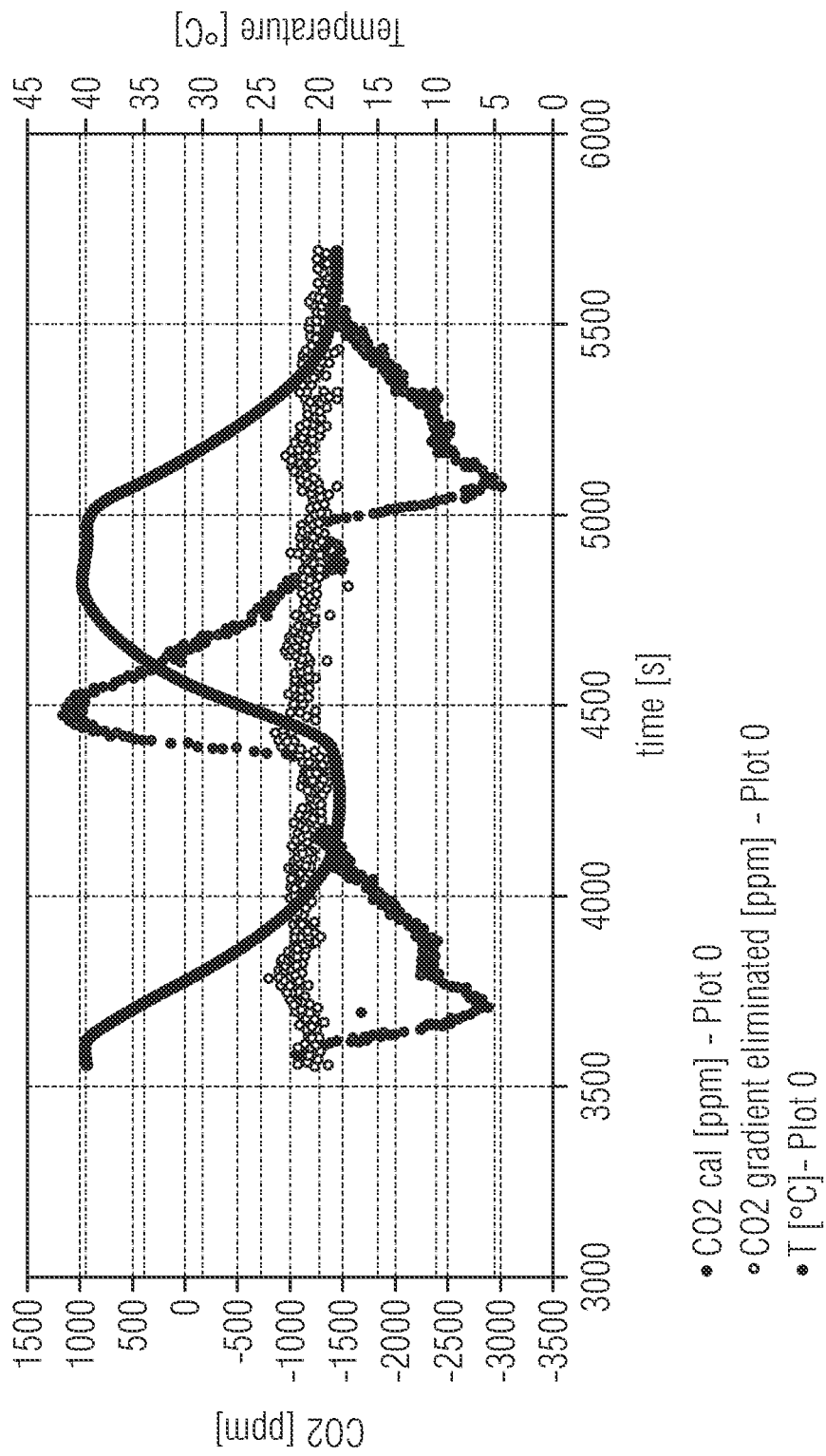
FIG. 4 shows the same data like shown in FIG. 2. The green curve shows results after applying the gradient correction.

FIG. 4 shows the same data like shown in FIG. 2. The green curve shows results after applying the gradient correction.

It is also possible to use e.g. different or better algorithms to compensate higher order gradient effects. E.g. if the sensor depends on the change of $T^2$. For example, a neuronal network can be used to automatically train for such kind of behaviors.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for compensating a temperature gradient effect for gas concentration sensors, the method comprising:
   variating a temperature gradient;
   measuring a variation of gas concentration depending on the variation of the temperature gradient;
   analysing a dependence of the gas concentration and the temperature gradient for setting up an error correction function; and
   applying the error correction function to correct measured values of the gas concentration.

2. The method of claim 1, wherein the error correction function is a linear function.

3. The method of claim 1, wherein the dependence of the gas concentration and the temperature gradient is analysed by a neuronal network.

4. A device comprising:
   a sensor configured to measure gas concentrations; and
   an analysing unit configured to:
      analyse a dependence of a gas concentration on a temperature gradient during calibration of the sensor in order to set up an error correction function; and
      apply the error correction function to measured values of the gas concentration after the calibration is completed,
   wherein the device is configured to measure the gas concentrations independent of the temperature gradient.

5. The device of claim 4, wherein the analysing unit comprises a neuronal network configured to analyse the dependence of the gas concentration on the temperature gradient.

* * * * *